United States Patent
Kobayashi et al.

(10) Patent No.: US 11,925,458 B2
(45) Date of Patent: Mar. 12, 2024

(54) MOTION STATE MONITORING SYSTEM, TRAINING SUPPORT SYSTEM, MOTION STATE MONITORING METHOD, AND PROGRAM

(71) Applicant: Toyota Jidosha Kabushiki Kaisha, Toyota (JP)

(72) Inventors: Makoto Kobayashi, Nisshin (JP); Toru Miyagawa, Seto (JP); Issei Nakashima, Toyota (JP); Keisuke Suga, Nagoya (JP); Masayuki Imaida, Ichinomiya (JP); Manabu Yamamoto, Toyota (JP); Yohei Otaka, Kariya (JP); Masaki Katoh, Nagoya (JP); Asuka Hirano, Toyota (JP); Taiki Yoshida, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 59 days.

(21) Appl. No.: 17/401,940

(22) Filed: Aug. 13, 2021

(65) Prior Publication Data
US 2022/0054045 A1  Feb. 24, 2022

(30) Foreign Application Priority Data
Aug. 18, 2020 (JP) ................................ 2020-138240

(51) Int. Cl.
 *A61B 5/11* (2006.01)
 *A61B 5/00* (2006.01)
 *G16H 40/63* (2018.01)

(52) U.S. Cl.
 CPC .......... *A61B 5/1114* (2013.01); *A61B 5/6831* (2013.01); *A61B 5/684* (2013.01);
 (Continued)

(58) Field of Classification Search
 CPC ....... A61B 5/1114; A61B 5/11; A61B 5/1121; A61B 5/1126; A61B 5/6831; A61B 5/684;
 (Continued)

(56) References Cited

U.S. PATENT DOCUMENTS

2014/0330172 A1* 11/2014 Jovanov ............... A61B 5/1116
                                                       600/595
2017/0003765 A1*  1/2017 Shedletsky ............. G06F 3/167
(Continued)

FOREIGN PATENT DOCUMENTS

JP   2006198073 A   8/2006
JP   2013106768 A   6/2013
(Continued)

OTHER PUBLICATIONS

Carson HJ, Richards J, Mazuquin B. Examining the influence of grip type on wrist and club head kinematics during the golf swing: Benefits of a local co-ordinate system. Eur J Sport Sci. Apr. 2019; 19(3):327-335. doi: 10.1080/17461391.2018.1508504. Epub Aug. 15, 2018. PMID: 30110244. (Year: 2018).*
(Continued)

*Primary Examiner* — Eric F Winakur
*Assistant Examiner* — Elina Sohyun Ahn
(74) *Attorney, Agent, or Firm* — Dinsmore & Shohl LLP

(57) ABSTRACT

A motion state monitoring system, a training support system, a motion state monitoring method, and a program capable of suitably managing measurement results according to an attaching direction of a sensor are provided. A motion state monitoring system according to the present disclosure monitors a motion state of a target part of a subject's body. The motion state monitoring system includes an acquisition unit, an attaching direction detection unit, and a control processing unit. The acquisition unit acquires sensing information of a sensor attached to the target part. The attaching direction detection unit detects an attaching direction of the sensor. The control processing unit outputs information related to the sensing information in association with the attaching direction.

11 Claims, 10 Drawing Sheets

(52) U.S. Cl.
CPC ............ G16H 40/63 (2018.01); *A61B 5/0004* (2013.01); *A61B 2505/09* (2013.01)

(58) Field of Classification Search
CPC ..... A61B 5/1107; A61B 5/1118; A61B 5/103; A63B 24/0062
See application file for complete search history.

(56) References Cited

U.S. PATENT DOCUMENTS

| | | | |
|---|---|---|---|
| 2017/0076619 A1* | 3/2017 | Wallach | ............. G09B 19/0038 |
| 2019/0117128 A1* | 4/2019 | Chen | ...................... A61B 5/683 |

FOREIGN PATENT DOCUMENTS

| | | | |
|---|---|---|---|
| JP | 2014208257 A | | 11/2014 |
| JP | 2020-081413 A | | 6/2020 |

OTHER PUBLICATIONS

Non-Final Office Action dated Mar. 20, 2023 in related U.S. Appl. No. 17/401,922.

Carson et al., Examining the influence of grip type on wrist and club head kinematics during the golf swing: Benefits of a local co-ordinate system, Eur J Sport Sci. Apr. 2019; 19(3):327-335. doi: 10.1080/17461391.2018.1508504. Epub Aug. 15, 2018. PMID: 30110244.

Final Office Action dated Jul. 31, 2023, Issued to related U.S. Appl. No. 17/401,922, filed Aug. 13, 2021.

* cited by examiner

| PART ID | PART | ANGLE $\theta_0$ (°) BETWEEN INITIAL REFERENCE DIRECTION D AND $Z_s$ AXIS |
|---|---|---|
| 1 | RIGHT UPPER ARM | 5 |
| 2 | RIGHT FOREARM | 10 |
| 3 | HEAD | 0 |
| 4 | CHEST | 0 |
| 5 | WAIST | 0 |
| 6 | LEFT UPPER ARM | −5 |
| 7 | LEFT FOREARM | −10 |
| 8 | RIGHT THIGH | 0 |
| 9 | RIGHT LOWER LEG | 0 |
| 10 | LEFT THIGH | 0 |
| 11 | LEFT LOWER LEG | 0 |

Fig. 3

| ATTACHING ANGLE $\theta_1$ (°) | CALCULATION ORDER OF ROTATION ANGLES |
|---|---|
| 0° | X AXIS→Z AXIS→Y AXIS |
| 90° | Y AXIS→Z AXIS→X AXIS |

Fig. 8

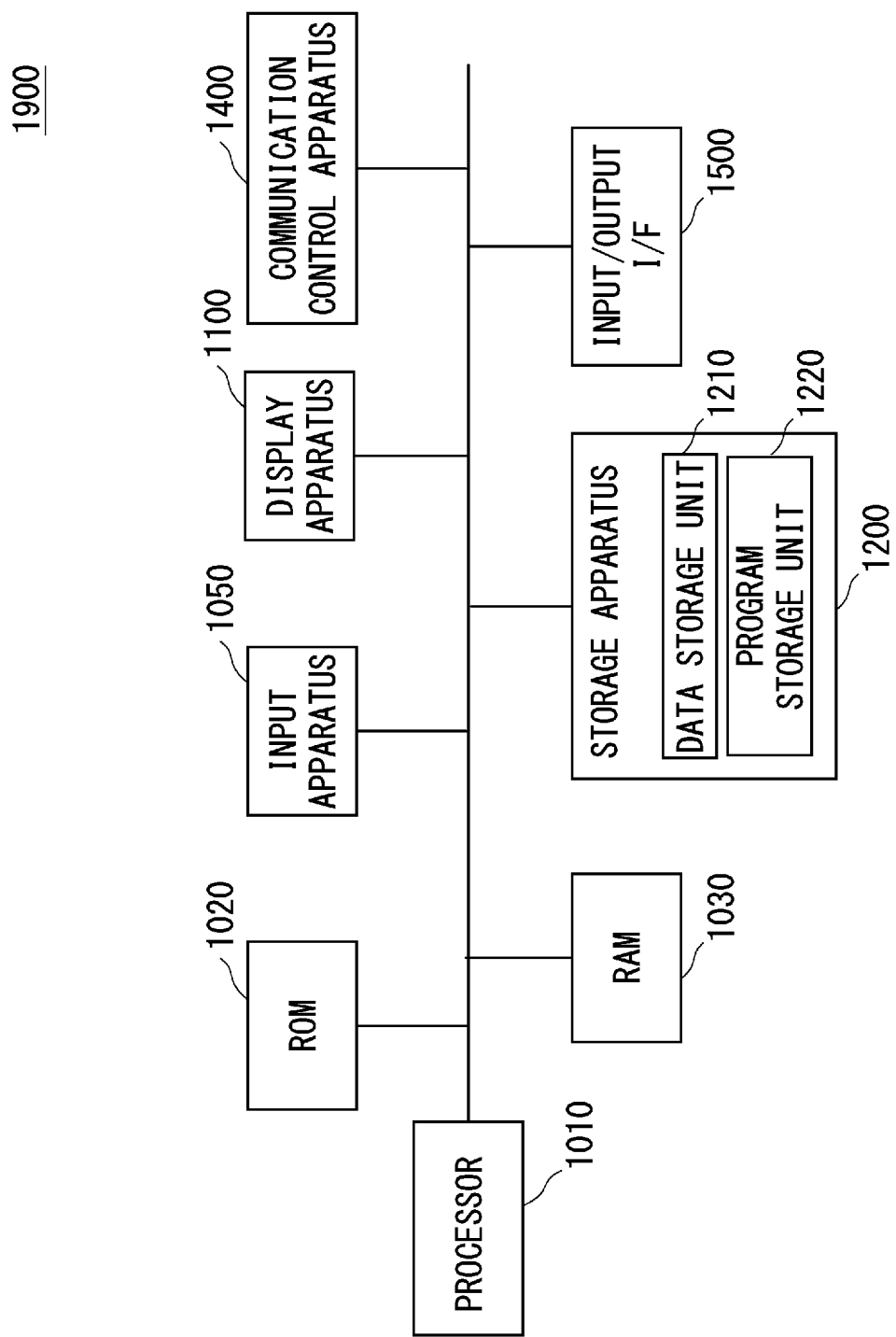

MOTION STATE MONITORING SYSTEM, TRAINING SUPPORT SYSTEM, MOTION STATE MONITORING METHOD, AND PROGRAM

CROSS REFERENCE TO RELATED APPLICATIONS

This application is based upon and claims the benefit of priority from Japanese patent application No. 2020-138240, filed on Aug. 18, 2020, the disclosure of which is incorporated herein in its entirety by reference.

BACKGROUND

The present disclosure relates to a motion state monitoring system, a training support system, a motion state monitoring method, and a program.

Motion tests to measure a motion function of rehabilitation trainees or the elderly are known. For example, Japanese Unexamined Patent Application Publication No. 2020-081413 discloses an operation detection system for detecting a motion state of a subject during the motion test using measurement data of a sensor attached to the subject's body part. In this motion detection system, the sensor is connected to a belt-like band, and the subject attaches the sensor to a target part by attaching the band to the target part.

SUMMARY

Here, there is a demand that the sensor be freely attached and the measurement results be managed separately for each attaching direction. However, in the system disclosed in Japanese Unexamined Patent Application Publication No. 2020-081413, the connection direction of the sensor with respect to the axial direction of the band is fixed, and thus the attaching direction of the sensor cannot be freely set. Therefore, there is a problem that it is not possible to manage the measurement results separately for each attaching direction.

There is also a similar problem in the management of measurement results when the sensor is attached to the subject's body part with clothing, an adhesive surface, or another connecting tool interposed therebetween.

The present disclosure has been made to solve such a problem and an object thereof is to provide a motion state monitoring system, a training support system, a motion state monitoring method, and a program capable of suitably managing measurement results according to an attaching direction of a sensor.

An example aspect of the embodiment is a motion state monitoring system for monitoring a motion state of a target part of a subject's body. The motion state monitoring system includes an acquisition unit configured to acquire sensing information of a sensor attached to the target part, an attaching direction detection unit configured to detect an attaching direction of the sensor, and a control processing unit configured to output information related to the sensing information in association with the attaching direction of the sensor. Thus, the motion state monitoring system can suitably manage the measurement result according to the attaching direction of the sensor.

The attaching direction of the sensor is an attaching direction of the sensor with respect to a direction predetermined according to the target part.

The attaching direction of the sensor may be an attaching direction of the sensor with respect to an axial direction of a band attached to the target part. Thus, the attaching direction of the sensor can be easily identified with reference to the band.

The control processing unit may be configured to, in response to detection of an event in which the attaching direction changes during measurement by the sensor, output the information related to the sensing information acquired after the event in association with the attaching direction detected after the event. Thus, even if the attaching direction is changed intentionally or unintentionally during the monitoring target motion, the motion state monitoring system can manage the subsequent measurement results in association with the changed attaching direction.

The control processing unit may be configured to execute arithmetic processing on the sensing information or information related to the sensing information according to the attaching direction, and output an arithmetic processing result in association with the attaching direction of the sensor. Thus, the motion state monitoring system can easily compare and use measurement results regardless of the attaching direction.

Another example aspect of the embodiment is a training support system including the above motion state monitoring system and measuring equipment including the sensor. Thus, the training support system can suitably manage the measurement result according to the attaching direction of the sensor.

The measuring equipment may include a changing member configured to change the attaching direction of the sensor. Thus, the attaching direction of the sensor can be freely set, thereby improving the convenience. Further, the accuracy of the sensing results of some sensors is improved by setting the attaching direction of the sensor in a suitable direction.

Another example aspect of the embodiment is a motion state monitoring method for monitoring a motion state of a target part of a subject's body. The motion state monitoring method includes steps of acquiring sensing information of a sensor attached to the target part, detecting an attaching direction of the sensor, and outputting information related to the sensing information in association with the attaching direction of the sensor.

Another example aspect of the embodiment is a motion state monitoring program for monitoring a motion state of a target part of a subject's body. The motion state monitoring program causes a computer to execute a process of acquiring sensing information of a sensor attached to the target part; a process of detecting an attaching direction of the sensor; and a process of outputting information related to the sensing information in association with the attaching direction of the sensor.

According to the present disclosure, it is possible to provide a motion state monitoring system, a training support system, a motion state monitoring method, and a program capable of suitably managing measurement results according to an attaching direction of a sensor.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 3 is a diagram for explaining an initial reference direction according to the first embodiment;

FIG. 8 shows an example of a data structure of arithmetic processing table according to a second embodiment;

FIG. 10 is a schematic configuration diagram of a computer according to this embodiment.

DETAILED DESCRIPTION

Although the present disclosure is described below through the embodiments, the disclosure according to the claims is not limited to the following embodiments. In addition, not all of the configurations described in the embodiments are indispensable as means for solving the problems. For clarity of description, the following descriptions and drawings have been omitted and simplified as appropriate. In each drawing, the same elements are denoted by the same reference signs.

First Embodiment

First, a first embodiment of the present disclosure will be described with reference to FIGS. 1 to 7.

Figure 1:
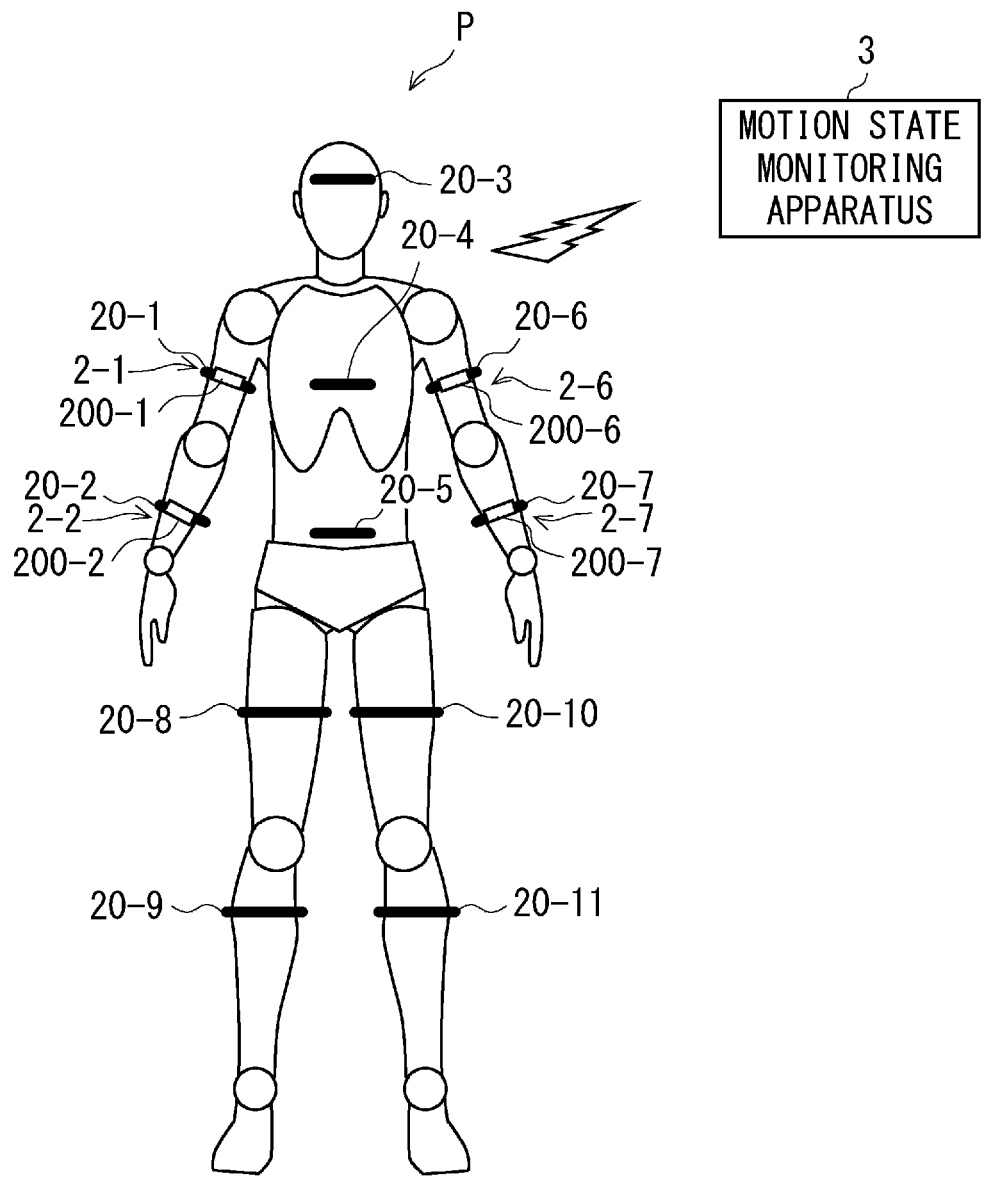
FIG. 1 is a schematic configuration diagram of a training support system according to a first embodiment.

FIG. 1 is a schematic configuration diagram of a training support system 1 according to a first embodiment. The training support system 1 is a computer system for supporting training by measuring a motion function of a subject P such as a rehabilitation trainee or an elderly person, and analyzing, evaluating, and managing measurement results. The subject P attaches a sensor to his/her body part and performs a motion test. For example, the motion test is a motor function test for measuring a motion state of a target part when the subject P takes a designated motion and measures the motion function.

Hereinafter, the designated motion may be referred to as a monitoring target motion. The monitoring target motion is determined corresponding to a body part. Examples of the monitoring target motion include flexion and extension of shoulder, adduction and abduction of shoulder, lateral and medial rotations of shoulder, flexion and extension of neck, medial rotation of neck, flexion and extension of elbow, lateral and medial rotation of hip, pronation and external rotation of forearm, and thoracolumbar lateral flexion. When the target part is either left or right body part, the monitoring target motion may be separately determined for the left or right body part. One or more parts may be associated with one monitoring target motion as the target parts, and the same part may be associated with different monitoring target motions as the target parts.

As shown in this drawing, the training support system 1 includes measuring equipment 2 and a motion state monitoring system (hereinafter referred to as a motion state monitoring apparatus) 3.

The measuring equipment 2 is a measuring apparatus that measures a moving direction and an amount of movement. In the first embodiment, the measuring equipment 2 includes an acceleration sensor and an angular velocity sensor, and measures its acceleration and angular velocity. Specifically, the measuring equipment 2 may include a triaxial acceleration sensor and a triaxial angular velocity sensor. In this case, the measuring equipment 2 measures the amounts of movement of the XYZ axes in the three-axis direction and the rotation angles around the three axes. The measurement axes are not limited to three axes, and instead may be two or less axes. The measuring equipment 2 may include a geomagnetic sensor for detecting geomagnetism and measuring a direction in which the measuring equipment 2 is oriented.

The measuring equipment 2 is connected to the motion state monitoring apparatus 3 so that communication is possible between them. In the first embodiment, the communication between the measuring equipment 2 and the motion state monitoring apparatus 3 is short-range wireless communication such as Bluetooth (registered trademark), NFC (Near Field Communication), and ZigBee. However, the communication may be wireless communication through a network such as a wireless LAN (Local Area Network). The communication may also be wired communication over a network constituted by the Internet, a LAN, a WAN (Wide Area Network), or a combination thereof.

The measuring equipment 2 includes sensors 200 and attaching structures of the sensors 200. The sensors 200 are attached to attaching positions 20 of target parts of the subject P's body with the attaching structures interposed therebetween. Each of the plurality of sensors 200 is associated with each of the body part of the subject P, and can be attached to the associated part, in order to measure the various monitoring target motions. In this drawing, attachable parts are shown by the attaching positions 20-1, 20-2, . . . and 20-11, which are associated with the sensors 200-1, 200-2, . . . and 200-11, respectively. For example, the attaching positions 20-1, 20-2, . . . and 20-11 are respectively referred to as a right upper arm, a right forearm, a head, a chest (trunk), a waist (pelvis), a left upper arm, a left forearm, a right thigh, a right lower leg, a left thigh, and a left lower leg. The associations between the attaching positions 20 and the sensors 200 are made by pairing between the sensors 200 and the motion state monitoring apparatus 3 in advance and associating identification information (ID) of the attaching positions 20 with the IDs of the sensors 200 in the application of the motion state monitoring apparatus 3.

In the first embodiment, the attaching position 20 used in the motion test is selected from the attaching positions 20-1 to 20-11 according to the monitoring target motion selected by a user. Note that the user is a user who uses the motion state monitoring apparatus 3, and is, for example, the subject P himself/herself or a staff member who performs the motion test. The subject P or the staff member then attaches the sensors 200 (in this drawing, 2-1, 2-2, 2-6, 2-7) associated with the selected attaching positions 20 (in this drawing, 20-1, 20-2, 20-6, 20-7) of the subject P's body and starts the motion test. The sensor 200 may be attached at a position other than the attaching positions 20-1 to 20-11 of the subject P's body.

Although the plurality of sensors 200 associated with the plurality of attaching positions 20, respectively, are prepared, the number of attaching positions 20 prepared may be one, and the number of sensors 200 prepared may also be one.

The sensor 200 starts measurement in response to the start of the motion test and transmits sensing information to the motion state monitoring apparatus 3. The sensing information may include acceleration information, angular velocity information, or quaternion information. The sensing information may include components in the respective measurement axis directions (X, Y, Z axis directions). The sensor 200 stops the measurement in response to the end of the motion test.

The motion state monitoring apparatus 3 is a computer apparatus which monitors the motion state of the target part of the subject P's body during the motion test, and analyzes, evaluates, and manages information about the motion state. Specifically, the motion state monitoring apparatus 3 may be a personal computer, a notebook-sized computer, a cellular phone, a smartphone, a tablet terminal, or any other communication terminal apparatus capable of inputting/outputting data. The motion state monitoring apparatus 3 may be a server computer. In the first embodiment, the motion state monitoring apparatus 3 will be described as a tablet terminal.

The motion state monitoring apparatus 3 is used by the user during the motion test and before and after the motion test. The motion state monitoring apparatus 3 receives the selection of the monitoring target motion from the user, and notifies the user of the attaching position 20 corresponding to the target part. The motion state monitoring apparatus 3 transmits a request for starting or stopping the measurement to the sensor 200 in response to the start or end of the motion test. The motion state monitoring apparatus 3 outputs sensing-related information as the measurement result in response to reception of the sensing information from the sensor 200. Here, the sensing-related information indicates information related to the sensing information, may include the sensing information itself, and may be information obtained by applying various conversion processing to the sensing information. The information about the motion state is based on the sensing-related information, and may include the sensing-related information itself.

The motion state monitoring apparatus 3 may be connected to an external server (not shown) through a network so that communication is possible between them. The external server may be a computer apparatus or a cloud server on the Internet. In this case, the motion state monitoring apparatus 3 may transmit the sensing-related information or information about the motion state of the subject P held by itself to the external server.

Figure 2:
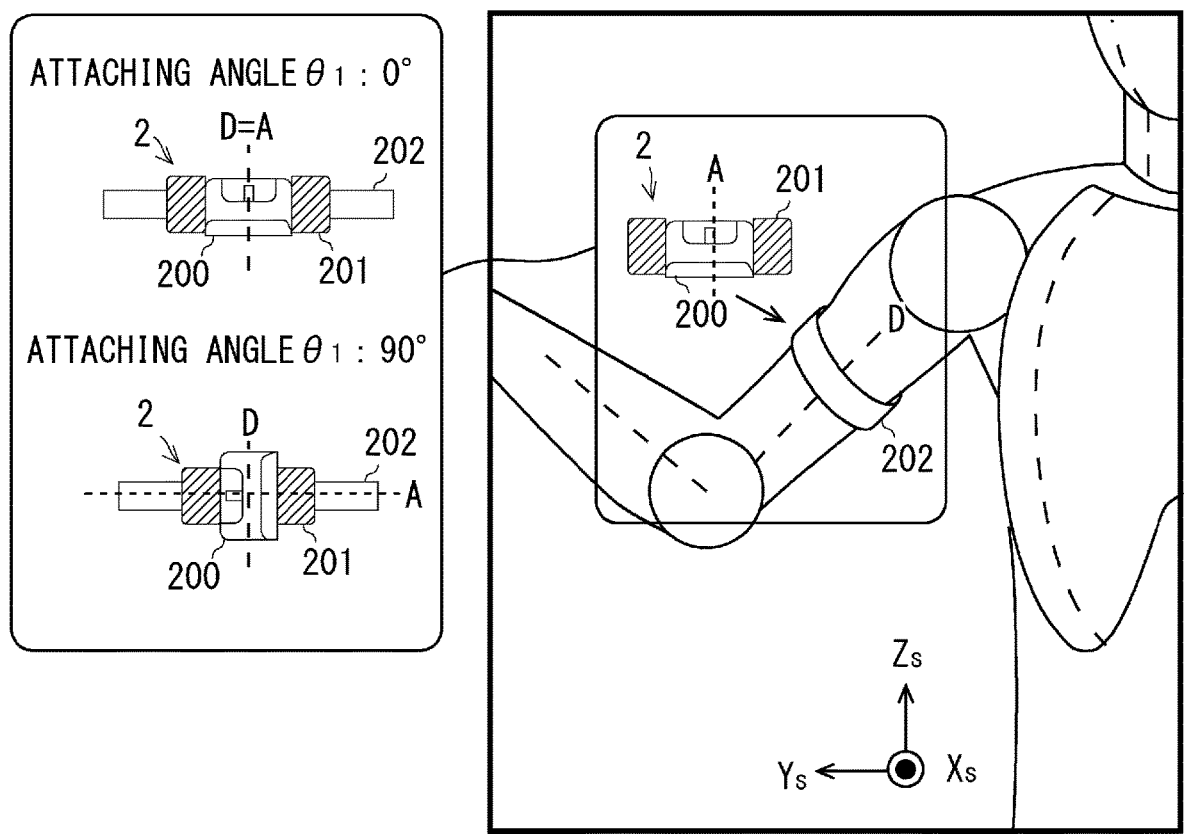
FIG. 2 is a diagram for explaining an example of attaching a sensor of measuring equipment according to the first embodiment.

The attachment of the sensor 200 of the measuring equipment 2 according to the first embodiment will now be described with reference to FIGS. 2 to 3. FIG. 2 is a diagram for explaining an example of the attachment of the sensor 200 of the measuring equipment 2 according to the first embodiment.

As shown in FIG. 2, the measuring equipment 2 includes the sensor 200, an attaching pad 201 and a belt-like band 202 as the attaching structure (an attachment tool). The sensor 200 is connected to the band 202 attached to the target part with an attaching pad 201 interposed therebetween. In this way, the sensor 200 is attached to the attaching position 20 of the target part. The connection member (the connecting tool) between the sensor 200 and the band 202 is not limited to the attaching pad 201, and may instead be a fastener such as a hook or snap or a hook-and-loop fastener.

An attaching direction of the sensor 200 will now be described. The attaching direction of the sensor 200 is the attaching direction of the sensor 200 with respect to a reference direction D. In the first embodiment, the reference direction D is a direction in which the attaching direction does not change relatively even if the target part is moved during the monitoring target motion. That is, the reference direction D is a direction that changes along with an absolute direction of the sensor 200 during the monitoring target motion. Here, the "absolute direction" is a direction based on the gravity direction or the horizontal direction, and may be, for example, a direction defined by a coordinate system $(X_S, Y_S, Z_S)$ with respect to the subject P. The $X_S$ axis is a horizontal axis in the longitudinal direction with respect to the subject P, the $Y_S$ axis is a horizontal axis in the lateral direction with respect to the subject P, and the $Z_S$ axis is a vertical axis in the gravity direction.

In FIG. 2, the reference direction D is defined as an axial direction of the band 202 attached to the target part. The attaching direction indicates a relative direction of the sensor 200 with respect to the reference direction D which is the axial direction. Specifically, the attaching direction is determined based on an angle $\theta_1$ (which is referred to as an attaching angle) formed by the reference direction D and a measurement axis A of the sensor. The measurement axis A may be predetermined and may be, for example, one of the X, Y, and Z axes of the sensor coordinate system. For example, as shown in FIG. 2, when the attaching angle $\theta_1$ is 0°, the sensor 200 is attached so that the measurement axis A becomes parallel to the reference direction D, while when the attaching angle $\theta_1$ is 90°, the sensor 200 is attached so that the measurement axis A becomes perpendicular to the reference direction D. Note that the attaching angle $\theta_1$ is not limited to 0° and 90°.

In the first embodiment, the reference direction D can be defined according to the target part. For example, when the band 202 is attached to the target part, there is a certain attaching direction for each target part. When the target part is, for example, an arm, the band 202 may be attached so that the reference direction D of the band 202 becomes substantially parallel to the axial direction of the arm (i.e., the direction in which the arm extends) in terms of ease of attachment and mobility. On the other hand, it is difficult to attach the sensor to the arm so that the reference direction D becomes substantially perpendicular to the axial direction of the arm. Therefore, the axial direction of the band 202 as the reference direction D can be defined in advance according to the target part.

In FIG. 2, although the sensor 200 is attached to the target part using the band 202, the band 202 may be omitted. In this case, the sensor 200 may be attached to the clothing or the skin with the attaching pad 201 interposed therebetween. Also in this case, the reference direction D is a direction defined in advance according to the target part, such as the axial direction of the target part.

In the first embodiment, the attaching structure of the measuring equipment 2 includes a changing member for changing the attaching direction of the sensor 200. The changing member may have any structure capable of changing the attaching direction of the sensor 200. For example, if the attaching pad 201 has an adhesive surface that can be used repeatedly, the attaching direction of the sensor 200 is freely changed. When the sensor 200 is attached to the target part using a connecting tool between the sensor 200 and the belt or clothing, after the sensor is attached in the direction substantially the same as the reference direction D, the attaching direction of the sensor may be changed using a knob or the like which moves together with the connecting tool. When the sensor 200 is attached using a connecting tool having a shape capable of holding the sensor 200 in a plurality of attaching directions, the sensor 200 may be attached in one of the attaching direction selected from the plurality of attaching directions.

In the first embodiment, the reference direction D can be specifically determined in advance according to the target part in the initial state, i.e., in a stationary state. FIG. 3 is a diagram for explaining the initial reference direction D according to the first embodiment. As shown in this drawing, the absolute direction of the initial reference direction D is determined for each part. In this drawing, the absolute direction of the initial reference direction D is expressed by an angle $\theta_0$ formed with respect to the $Z_S$ axis. The angle $\theta_0$ may be determined based on an average human skeleton. In this example, the initial reference direction D of the upper arm is directed outward with respect to the $Z_S$ axis. For example, the angle $\theta_0$ of the right upper arm may be determined to be 5°. Further, the initial reference direction D of the forearm is directed more outward with respect to the $Z_S$ axis than the upper arm. For example, the angle $\theta_0$ of the right forearm may be determined to be 10°. The angle $\theta_0$ for each part may be determined for each subject P based on attribute information such as age, sex, height, or weight of the subject P. In this manner, even when the initial reference direction D is changed according to the target part, since the initial reference direction D is specifically defined, at least the initial attaching direction can be converted into the absolute direction which is a primary index for the subject P.

As described above, the sensor 200 according to the first embodiment is configured so that the attaching direction can be changed. Thus, the user can freely set the attaching direction of the sensor 200, which improves the convenience. The accuracy of the measurement result of some sensors 200 is improved by setting such sensors 200 in a suitable direction.

Hereinafter, the attaching direction with respect to the reference direction D is simply referred to as an "attaching direction".

Figure 4:
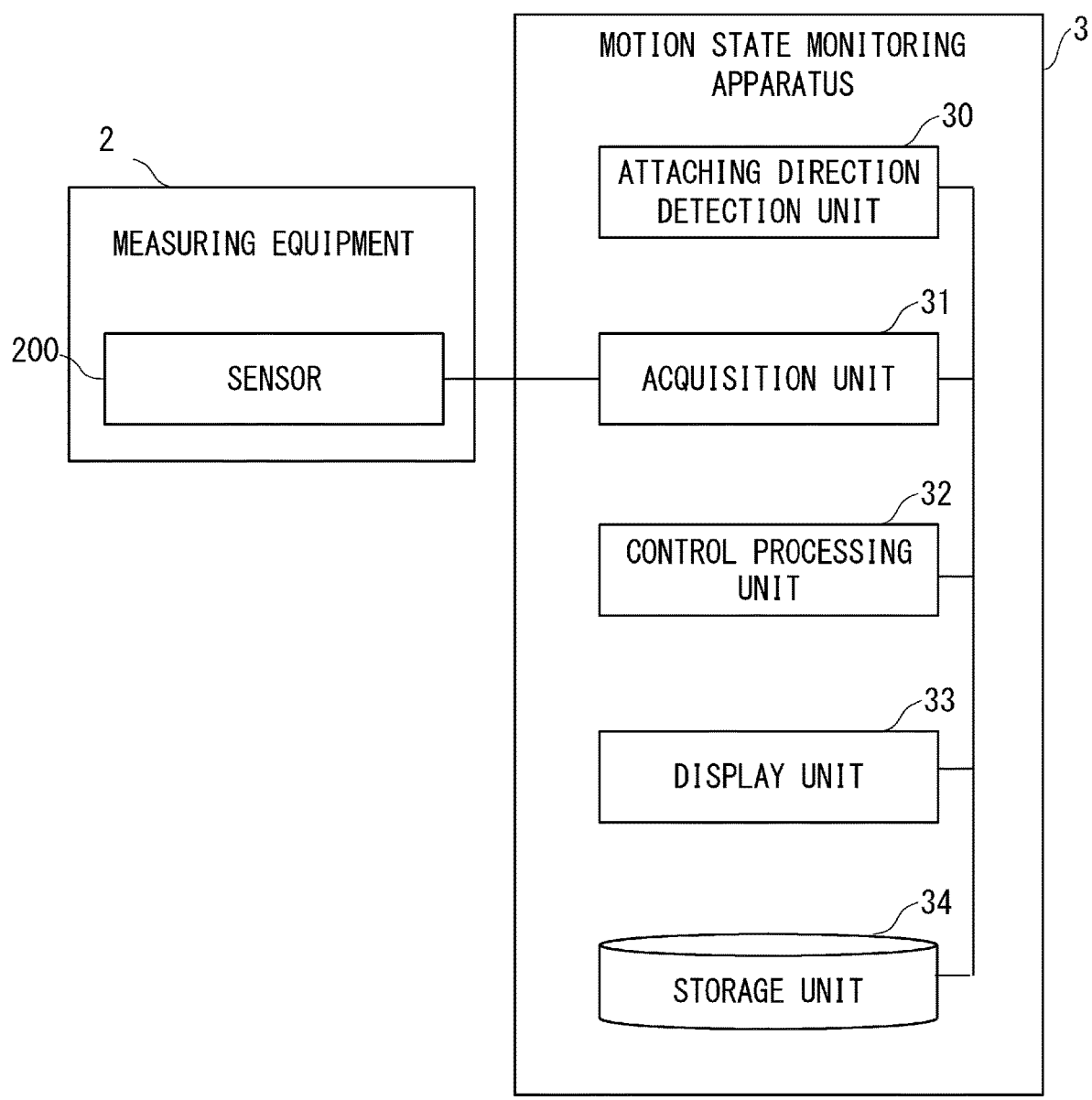
FIG. 4 is a block diagram showing an example of a configuration of the training support system according to the first embodiment.

FIG. 4 is a block diagram showing an example of the configuration of the training support system 1 according to the first embodiment. As described above, the training support system 1 includes the measuring equipment 2 and the motion state monitoring apparatus 3. The measuring equipment 2 includes the sensor 200. In this drawing, the sensor 200 is the sensor 200 that is associated with the attaching position 20 selected based on the monitoring target motion among the sensors 200-1 to 200-11. It is assumed that the sensor 200 is paired with the motion state monitoring apparatus 3 for wireless communication and calibrated in advance. The number of the sensors 200 is not limited to one, and instead may be two or more.

The motion state monitoring apparatus 3 includes an attaching direction detection unit 30, an acquisition unit 31, a control processing unit 32, a display unit 33, and a storage unit 34.

The attaching direction detection unit 30 detects the attaching direction of the sensor 200. For example, the attaching direction detection unit 30 may detect the attaching direction of the sensor 200 based on the output of the sensor 200 at the time of attaching. In this case, the attaching direction detection unit 30 calculates an attaching angle with respect to the $Z_S$ axis based on the information about the $Z_S$ axis acquired from the sensor 200 at the time of calibration and the information on the angle of the sensor 200 between the stationary state at the time of calibration and the time of mounting. In this manner, the attaching direction detection unit 30 can detect the attaching direction of the sensor 200.

For example, the attaching direction detection unit 30 may include an attaching direction detection sensor and an attaching direction detection mechanism separately provided in the vicinity of each sensor 200. The attaching direction detection mechanism is configured so that a current flows according to an angle between the measurement axis A of the sensor 200 and the reference direction D. The attaching direction detection sensor detects the current. The attaching direction is detected according to a magnitude of the detected current. When the band 202 is used for attaching the sensor 200, the attaching direction detection sensor and the attaching direction detection mechanism may be provided in the band 202. The attaching direction detection sensor and the attaching direction detection mechanism may be included in the measuring equipment 2, and the attaching direction detection unit 30 may acquire information about the attaching direction based on an output from the attaching direction detection sensor.

For example, the attaching direction detection unit 30 may detect the attaching direction of the sensor 200 based on a photographed image of the attached sensor 200. For example, the attaching direction detection unit 30 may include an attaching direction detection camera provided in front of, behind, or above the subject P. The attaching direction detection unit 30 may photograph the sensor 200 and performs image processing such as pattern matching on the photographed image to thereby detect the attaching direction of the sensor 200. The attaching direction detection camera may be included in the measuring equipment 2, and the attaching direction detection unit 30 may acquire the image from the attaching direction detection camera and acquire information about the attaching direction based on the image.

When the attaching direction of the sensor 200 can be adjusted by a knob or the like which moves together with the connecting tool, the attaching direction detection unit 30 may detect the attaching direction based on the moving amount of the knob.

In the first embodiment, the attaching direction detection unit 30 detects the attaching direction of the sensor 200 in an initial state, i.e., in a stationary state immediately before the measurement. The attaching direction detection unit 30 supplies the detected attaching direction information to the control processing unit 32.

The acquisition unit 31 acquires the sensing information of the sensor 200. In the first embodiment, the acquisition unit 31 receives and acquires the sensing information from the sensor 200. However, the acquisition unit 31 may indirectly acquire the sensing information from an external computer (not shown) that holds the sensing information. The acquisition unit 31 supplies the acquired sensing information to the control processing unit 32.

The control processing unit 32 controls each component of the sensor 200 and the motion state monitoring apparatus 3. The control processing unit 32 executes tagging processing for associating the attaching direction of the sensor 200 with the sensing-related information in the attaching direction. Then, the control processing unit 32 outputs, through the output unit, the sensing-related information which has been subjected to the tagging processing in which the sensing-related information is associated with the attaching direction of the sensor 200. The control processing unit 32 may store, in the storage unit 34, the sensing-related information which has been subjected to the tagging processing.

The display unit 33 is an example of an output unit and is a display for displaying the sensing-related information supplied from the control processing unit 32. In the first embodiment, the display unit 33 may be a touch panel constituted together with an input unit (not shown). The output unit may include, instead of or in addition to the display unit 33, an audio output unit for outputting the sensing-related information in audio, a data output unit for outputting the sensing-related information in a predetermined data format, or a transmission unit for transmitting the sensing-related information to an external server or the like.

The storage unit 34 is a storage medium for storing information necessary for performing various processes of the motion state monitoring apparatus 3. The storage unit 34 may store the sensing-related information which has been subjected to the tagging processing, but this is not essential if the output unit includes a transmission unit.

Figure 5:
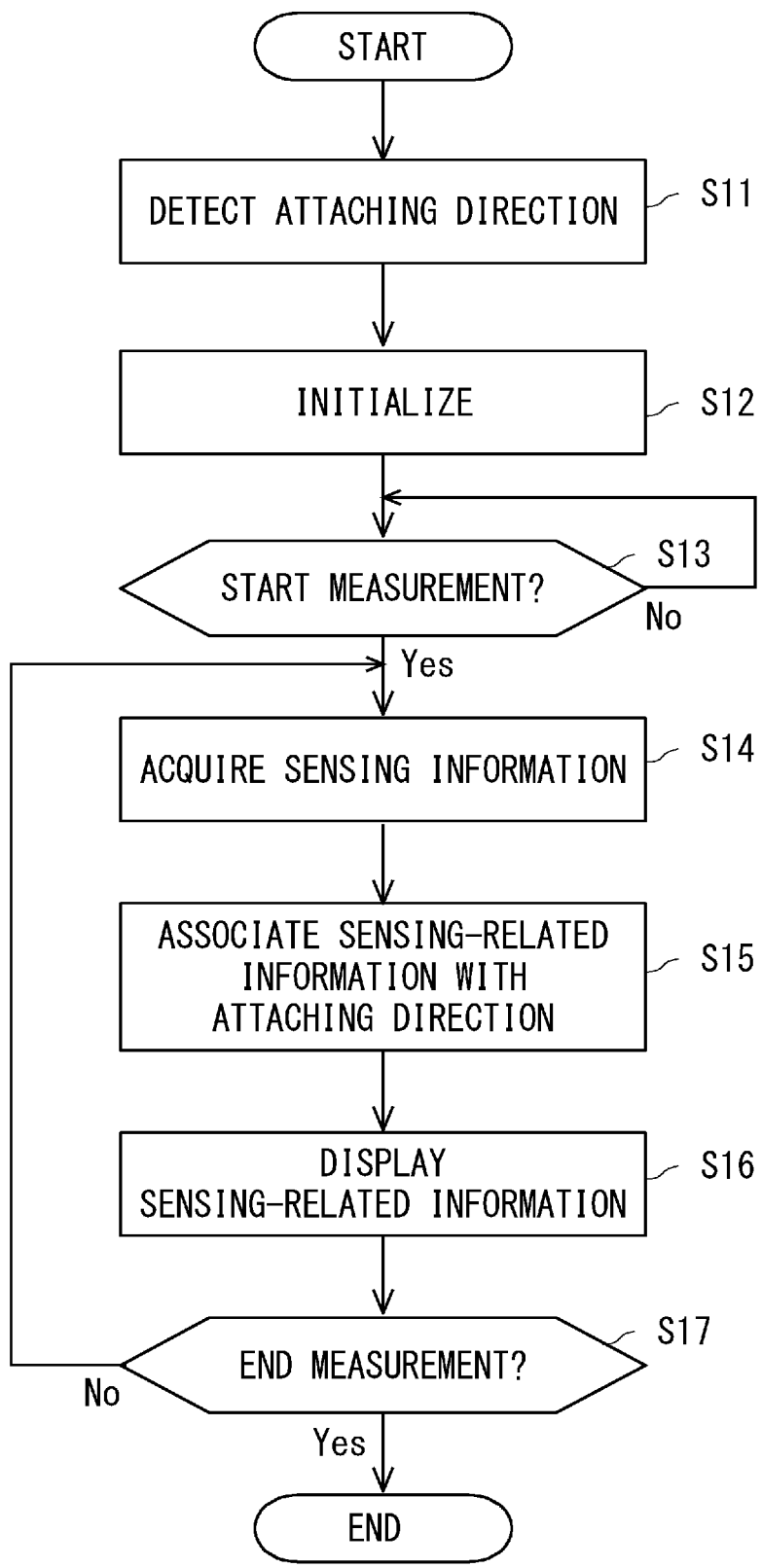
FIG. 5 is a flowchart showing an example of a processing procedure of a motion state monitoring apparatus according to the first embodiment.
Figure 6:
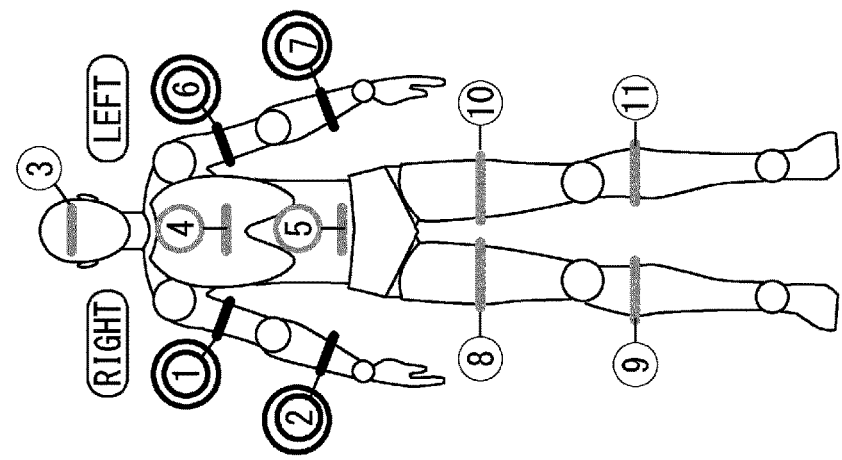
FIG. 6 shows an example of a display screen of a display unit according to the first embodiment before measurement is started.
Figure 7:
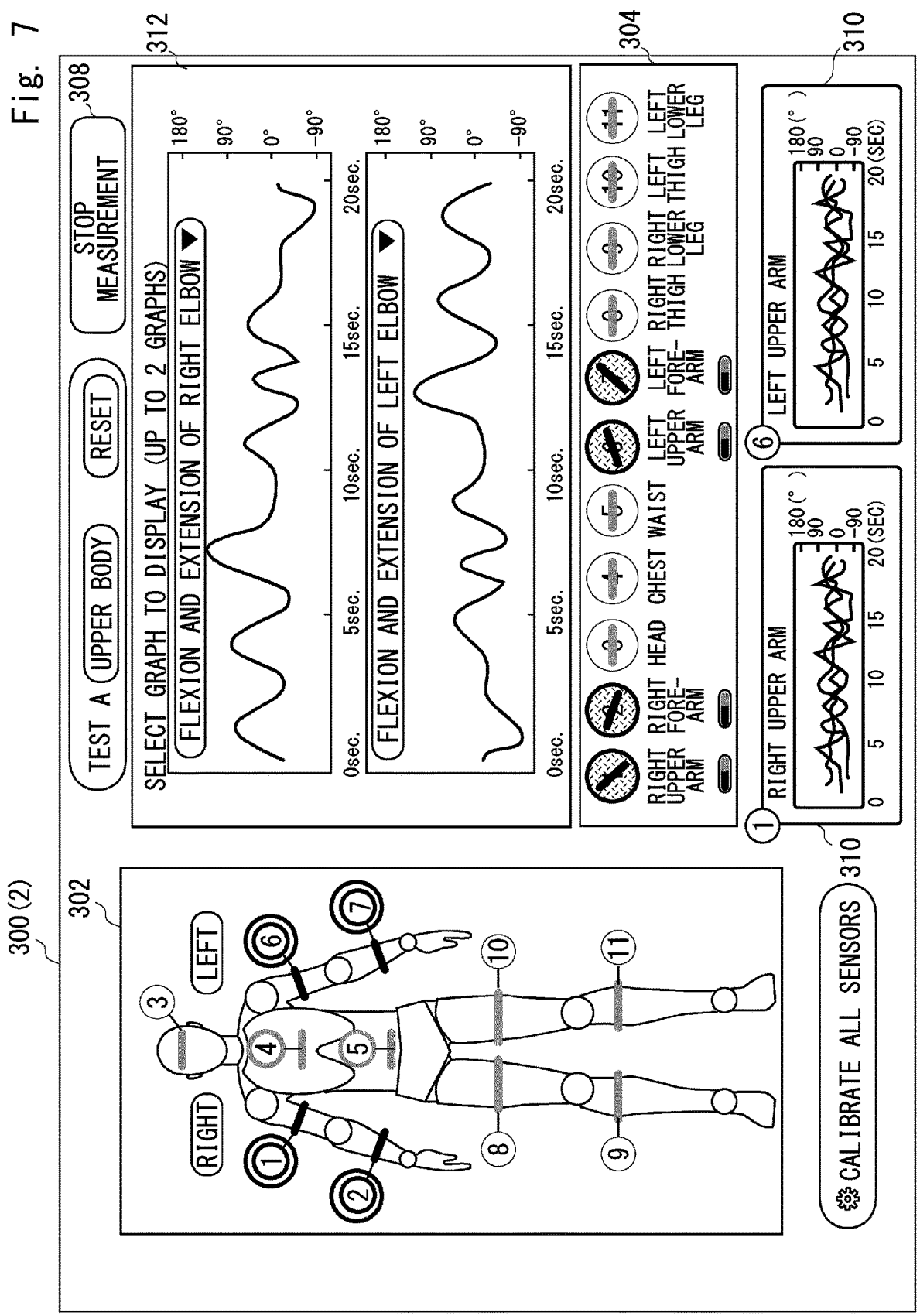
FIG. 7 shows an example of the display screen of the display unit according to the first embodiment when the measurement is ended.

Next, using FIG. 5, a motion state monitoring method according to the first embodiment will be described with reference to FIGS. 6 and 7. FIG. 5 is a flowchart showing an example of a processing procedure of the motion state monitoring apparatus 3 according to the first embodiment. FIG. 6 shows an example of a display screen of the display unit 33 according to the first embodiment before the measurement is started. FIG. 7 shows an example of a display screen of the display unit 33 according to the first embodiment when the measurement is ended.

The step shown in FIG. 5 starts when the monitoring target motion is selected by the user, the attaching position 20 is determined based on the monitoring target motion, and the sensor 200 is attached at the attaching position 20 corresponding to the monitoring target motion. In the following example, the control processing unit 32 treats the sensing information as the sensing-related information.

First, the attaching direction detection unit 30 of the motion state monitoring apparatus 3 detects the attaching direction of the sensor 200 by the user in response to the state of the subject P and the sensor 2 becoming stationary (Step S11). Next, the control processing unit 32 initializes the output value of the sensor 200 (Step S12). Specifically, the control processing unit 32 corrects the output value of the sensor 200 in the stationary state right before the measurement to 0. Even when the calibration is performed, the sensor 200 cannot set an output error such as a drift error to 0, and the error expands according to the elapsed time. Therefore, the output error from the start of the measurement to the end of the measurement can be minimized by this step. However, if the output error is slight, this step may be omitted. Then, the control processing unit 32 determines whether the measurement by the sensor 200 is to be started (Step S13). When the control processing unit 32 starts the measurement by the sensor 200 (Yes in Step S13), the processing advances to Step S14, while when the control processing unit 32 does not start the measurement by the sensor 200 (No in Step S13), the processing shown in Step S13 is repeated.

FIG. 6 shows a display image 300 (1) displayed by the display unit 33 before the measurement is started. The display image 300 (1) includes a plurality of display areas 302 to 306.

In the display area 302, icon images representing a plurality of attaching positions 20 as attaching candidates of the sensors 200 are displayed. In the display area 302, the attaching positions 20 (positions indicated by "1", "2", "6", and "7" in this drawing) corresponding to the selected measurement motion may be highlighted. Since the user can easily recognize the attaching positions 20 visually, the motion test can be smoothly performed.

When the user clicks the icon image representing the attaching position 20 of the display area 302, an image (not shown) indicating the attaching direction of the sensor 200 associated with the attaching position 20 is displayed. Thus, the user can easily understand the attaching direction of each sensor 200 through the input image.

In the display area 304, the rotation angles of the respective sensors 200-1, 200-2, . . . and 200-11 associated with the respective attaching position 20-1, 20-2, . . . and 20-11 are two-dimensionally displayed. The rotation angles displayed here dynamically change according to the movement of the sensors 200 which moves together with the subject P's motion. Thus, the user can identify, on the display area 304, the sensor 200 that is powered off and the sensor 200 that is not operating normally before starting the measurement.

Alternatively, the display area 304 may visually display the attaching directions of the sensors 20-1, 20-2, . . . and 20-11 associated with the attaching positions 200-1, 200-2, . . . and 200-11. Thus, the user can intuitively understand the attaching direction of each sensor 200 in the display area 304.

When the plurality of sensors 200 are used for the motion test, an input operation button for collectively calibrating the plurality of sensors 200 is displayed in the display area 305. This allows the user to easily request the calibration to each of the plurality of sensors 200 through the display area 305.

An input operation button for starting the motion test, i.e., for starting the measurement by the sensors 200, is displayed in the display area 306. This allows the user to easily request the start of the measurement by the sensors 200 through the display area 306.

In Step S14 shown in FIG. 5, the control processing unit 32 acquires the sensing information from the sensor 200 through the acquisition unit 31. The control processing unit 32 uses the sensing information as the sensing-related information, and adds information about the attaching direction of the sensor 200 to the sensing-related information as a tag, thereby associating the attaching direction with the sensing-related information (Step S15). The control processing unit 32 supplies the sensing-related information which has been subjected to the tagging processing to the display unit 33 and controls the display unit 33 to display it (Step S16). Then, the control processing unit 32 determines whether or not to end the measurement by the sensor 200 (Step S17). When the measurement is to be ended (Yes in Step S17), the control processing unit ends the processing, while when the measurement is not to be ended (No in Step S17), the control processing unit 32 returns the processing to Step S14.

Note that in the above example, the motion state monitoring apparatus 3 waits for the processing of Step S12, and then determines whether or not to start the measurement by the sensor 200 in Step S13. Alternatively, the motion state monitoring apparatus 3 may execute the processing of Step S12 in response to the determination that the measurement by the sensor 200 is to be started after the processing of Step S11 (Yes in Step S13). In this case, the control processing unit 32 may proceed the processing to Step S14 after the processing of Step S12 is executed or in parallel with the execution of the processing of Step S12. If the motion state monitoring apparatus 3 does not start the measurement by the sensor 200 (No in Step S13), the processing shown in Step S13 may be repeated.

In the above example, the motion state monitoring apparatus 3 uses the sensing information as the sensing-related information, and instead may use the sensing information subjected to various conversion processing instead of or in addition to the sensing information. This conversion processing may include conversion processing of quaternion information into rotation angles around X, Y, and Z axes. The rotation angle around the $X_S$ axis indicates a roll angle, the rotation angle around the $Y_S$ axis indicates a pitch angle, and the rotation angle around the $Z_S$ axis indicates a yaw angle. The control processing unit 32 calculates the rotation angles around the X, Y, and Z axes of a sensor coordinate system using quaternion information and converts them into the yaw angle, the roll angle, and the pitch angle, respectively. The conversion processing may also include graph normalization, standardization, or synthesis processing. In this case, instead of or in addition to the Step S15, the control processing unit 32 may impart information about the attaching direction of the sensor 200 as a tag to the sensing information which has been subjected to the conversion processing, and associate the attaching direction with the sensing information which has been subjected to the conversion processing.

FIG. 7 shows a display image 300 (2) displayed by the display unit 33 at the end of the measurement. The display image 300 (2) includes a plurality of display areas 302 to 312. The display areas 302 and 304 of the display image 300 (2) are similar to the display areas 302 and 304 of the display image 300 (1) shown in FIG. 6, respectively.

The attaching direction of each used sensor 200 may be displayed in the vicinity of the icon image representing the attaching position 20 of the display area 302, or may be displayed in response to the user clicking the icon image. Thus, the user can intuitively understand the attaching direction of the used sensor 200.

The display area 308 displays an input operation button for ending the motion test, i.e., for stopping the measurement by the sensor 200. Thus, the user can easily request to stop the measurement by the sensor 200 through the display area 308.

The sensing-related information of each used sensor 200 is displayed in the display area 310. In this drawing, the rotation angles around the $X_S$, $Y_S$ and $Z_S$ axial directions based on the outputs of some of the sensors 200-1 and 200-6 among the used sensors 200-1, 200-2, 200-6, and 200-7 are displayed in time series. Therefore, the display area 310, together with the display area 304, outputs the sensing-related information associated with the attaching direction of the used sensor 200 by display, so that the user can understand an attaching condition and the measurement result in association with each other. In this manner, the user can analyze, evaluate, or use the measurement results separately for each attaching condition.

The display area 312 displays a motion state index of the target part for each monitoring target motion performed. The motion state index is an index indicating the motion state of the target part when the monitoring target motion is performed. The control processing unit 32 calculates the motion state index of the target part based on the sensing-related information of the sensor 200. For example, when the monitoring target motion is "flexion and extension of right elbow", the sensing-related information of the sensors 20-1 and 20-2 at the attaching positions 200-1 and 200-2 is used. In this case, the control processing unit 32 may calculate the motion state index based on the difference between the sensing-related information of the sensor 200-1 and that of the sensor 200-2. Specifically, the control processing unit 32 calculates a three-dimensional rotation angle as the motion state index based on the difference between the quaternion information of the sensor 200-1 and that of the sensor 200-2. In this case, the rotation angles are calculated in the order of Z axis→Y axis→X axis and converted into the rotation angle around $X_S$, $Y_S$, and $Z_S$ axes, respectively. The calculation order of the rotation angles may be predetermined in accordance with the monitoring target motion. In this drawing, in the display area 312, time-series motion state indexes for some of the monitoring target motions are displayed among the performed monitoring target motions.

As described above, according to the first embodiment, the motion state monitoring apparatus 3 outputs the attaching direction of the sensor 200 in association with the measurement result. Therefore, the motion state monitoring apparatus 3 can appropriately manage the measurement result according to the attaching direction of the sensor 200, thereby improving the convenience.

Since the motion state monitoring apparatus 3 automatically detects the initial attaching direction of the sensor 200, it is possible to appropriately set the attaching direction at the time of attachment according to the preference of the subject P or the staff member, and to easily associate the attaching direction with the measurement result.

Second Embodiment

Next, a second embodiment of the present disclosure will be described. The second embodiment is characterized in that arithmetic processing is performed on the measurement result according to the attaching direction. Since a training support system 1 according to the second embodiment has the same configuration and functions as those of the training support system 1 according to the first embodiment, the description thereof will be omitted.

The control processing unit 32 of the motion state monitoring apparatus 3 of the training support system 1 executes arithmetic processing on the sensing information or sensing-related information according to the attaching direction. The arithmetic processing may be, for example, arithmetic processing for canceling, preventing, or minimizing the influence of the attaching direction when the sensing-related information becomes different according to the attaching direction even when the target part is moved in the same manner in the same monitoring target motion. In particular, when the control processing unit 32 calculates the rotation angles around the X, Y, and Z axes using the quaternion information and converts the calculated rotation angles into the rotation angles around the $X_S$, $Y_S$, and $Z_S$ axes, respectively, it is necessary to convert the four-dimensional vector data into three-dimensional data. In this arithmetic processing, there is a problem that the obtained rotation angles may become different depending on the order in which the rotation angles around the respective axes are calculated, so that the respective results of the calculations of these rotation angles cannot be compared with each other. In order to prevent or minimize such an influence, the calculation order of the rotation angles may be predetermined. Since the order of calculating the rotation angles depends on the attaching direction of the sensor 200, it is effective to determine the calculation order according to the attaching direction of the sensor 200.

Thus, in the second embodiment, the control processing unit 32 executes the arithmetic processing using an arithmetic processing table 320 that defines the arithmetic processing modes according to the attaching direction. Then, the control processing unit 32 controls the output unit to output the arithmetic processing result in association with the initial attaching direction of the sensor 200.

FIG. 8 shows an example of a data structure of the arithmetic processing table 320 according to the second embodiment. As shown in this drawing, the arithmetic processing table 320 is a table for associating the attaching angle $\theta_1$ with the calculation order of the rotation angles. The arithmetic processing table 320 defines that, for example, when the attaching angle $\theta_1$ is 0°, the rotation angles around the respective axes are calculated in the order of the X axis→the Z axis→the Y axis. When the attaching angle $\theta_1$ is 90°, the arithmetic processing table 320 defines the rotation angles around the respective axes are calculated in the order of Y axis→Z axis→X axis. By referring to the arithmetic processing table 320, the control processing unit 32 can easily execute preferable arithmetic processing according to the attaching direction.

The arithmetic processing table 320 defines the calculation order of the rotation angles according to the attaching direction of the sensor 200. Alternatively, the arithmetic processing table 320 may define the calculation order of the rotation angles according to the attaching direction and the target part or the monitoring target motion.

The arithmetic processing table 320 may include an arithmetic parameter used for the arithmetic processing in place of or in addition to the calculation order of the rotation angles. In this case, the arithmetic parameter may be a constant determined according to the attaching angle $\theta_1$, or may include a predetermined function having the attaching direction $\theta_1$ as a variable.

As described above, according to the second embodiment, the control processing unit 32 can easily compare and use a plurality of measurement results regardless of the attaching direction of the sensor 200. The second embodiment achieves the same effects as those of the first embodiment.

Third Embodiment

Next, a third embodiment of the present disclosure will be described with reference to FIG. 9. The third embodiment is characterized in that the attaching direction of the sensor 200 is detected not only in the initial state but also during the monitoring target motion. Since the motion state monitoring apparatus 3 according to the third embodiment has the same configuration as the motion state monitoring apparatus 3 according to the first or second embodiment, the description thereof will be omitted. However, in the motion state monitoring apparatus 3 according to the third embodiment, the attaching direction detection unit 30 detects the attaching direction during the measurement by the sensor 200 in addition to the initial state. In the motion state monitoring apparatus 3 according to the third embodiment, in response to detection of an event in which the attaching direction changes during the measurement by the sensor 200, the control processing unit 32 outputs the sensing-related information after the event in association with the attaching direction after the event.

Figure 9:
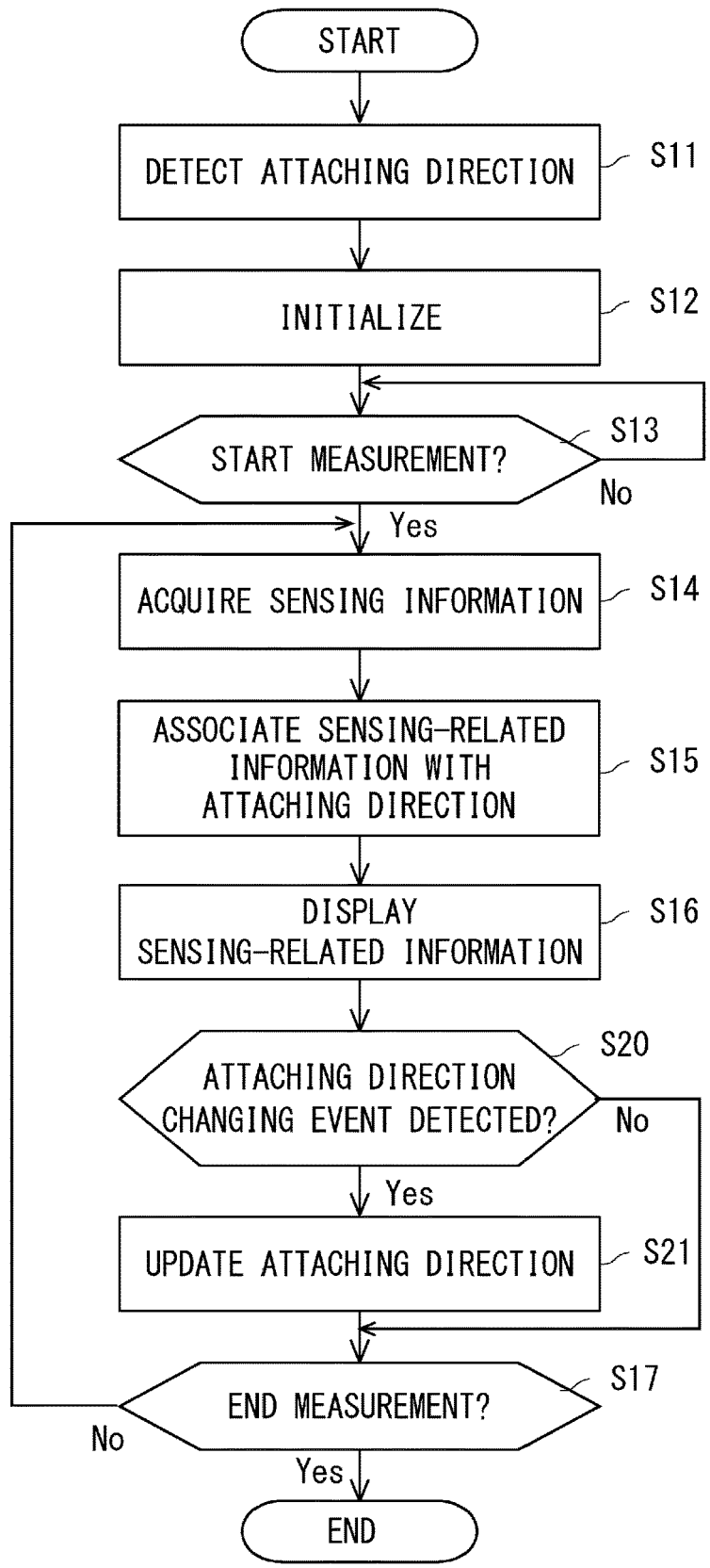
FIG. 9 is a flowchart showing an example of a processing procedure of a motion state monitoring apparatus according to a third embodiment.

FIG. 9 is a flowchart showing an example of a processing procedure of the motion state monitoring apparatus 3 according to the third embodiment. The steps shown in this drawing further include Step S20 and S21 in addition to the steps shown in FIG. 5. The steps similar to those shown in FIG. 5 are denoted by the same reference signs, and thus description thereof is omitted.

In response to the display unit 33 displaying the sensing-related information in Step S16, the attaching direction detection unit 30 determines whether or not the attaching direction changing event has been detected (Step S20). For example, when the subject P intentionally changes the attaching direction during the monitoring target motion, or when the attaching direction of the sensor 200 is unintentionally changed during the monitoring target motion, the attaching direction changing event is detected. More specifically, the attaching direction detection unit 30 may determine that the attaching direction changing event has been detected when a difference of attaching directions between before and after a certain timing, namely, the difference of the attaching angle $\theta_1$, is equal to or greater than a predetermined threshold. The detection of the attaching direction at this time may be performed in the same manner as the detection of the initial attaching direction. Alternatively, the attaching direction detection unit 30 may detect the attaching direction changing event from a temporal change of the sensing-related information. For example, when a discontinuous change of a predetermined threshold or more is detected in time-series information of the sensing-related information, the attaching direction detection unit 30 may determine that the attaching direction changing event has been detected. Whether or not the change is discontinuous may be determined based on whether the difference of the sensing-related information between before and after a certain timing is greater than the predetermined threshold or more than a predicted value.

When the attaching direction detection unit 30 determines that the attaching direction changing event has been detected (Yes in Step S20), the processing proceeds to Step S21, while when the attaching direction detection unit 30 does not determine that the attaching direction changing event has been detected (No in Step S20), the processing proceeds to Step S17.

In Step S21, the control processing unit 32 updates the attaching direction of the sensor 200 to be associated with the information related to the sensing information acquired after the attaching direction changing event into the attaching direction detected after the attaching direction changing event. Then, the control processing unit 32 proceeds the processing to Step S17.

As described above, according to the third embodiment, the motion state monitoring apparatus 3 detects the change during the measurement of the attaching direction of the sensor 200, and outputs the attaching direction after the change in association with the sensing-related information. Therefore, even if the attaching direction is changed intentionally or unintentionally during the monitoring target motion, the motion state monitoring apparatus 3 can manage the subsequent measurement results in association with the changed attaching direction. The third embodiment achieves the same effects as those of the first or second embodiments.

Note that the present disclosure is not limited to the above-described embodiments, and may be appropriately modified without departing from the scope of the disclosure. For example, other embodiments include the following embodiments.

Another First Embodiment

In the first embodiment, the control processing unit 32 of the motion state monitoring apparatus 3 performs control to output the sensing-related information in association with the attaching direction of the sensor 200 with respect to the reference direction D. However, the control processing unit 32 may convert the relative attaching direction detected from the user into the absolute direction and perform control to output the sensing-related information in association with the absolute direction instead of or in addition to the attaching direction.

For example, the control processing unit 32 can calculate an initial attaching angle $\theta_1'$ between the measurement axis A and the $Z_S$ axis by adding the angle $\theta_0$ between the initial reference direction D and the $Z_S$ axis shown in FIG. 3 to the detected initial attaching direction Oi of the sensor 200. The control processing unit 32 outputs the initial attaching angle $\theta_1'$ as information indicating the absolute direction of the sensor 200 in association with the sensing-related information. Note that the absolute direction of the sensor 200 during the measurement can be calculated based on the initial absolute direction of the sensor 200, the rotation angle of the sensor 200 as the measurement result of the sensor 200, and the amount of change in the attaching angle during the measurement. In this manner, the user can analyze the measurement result in consideration of more detailed measurement condition, thereby improving the analysis accuracy.

Another Second Embodiment

In the second embodiment, the control processing unit 32 of the motion state monitoring apparatus 3 executes the arithmetic processing on the sensing information or the sensing-related information according to the attaching direction. Alternatively or additionally, the control processing unit 32 may execute the arithmetic processing on the sensing information or the sensing-related information according to the absolute direction of the sensor 200. In this case, the arithmetic processing table 320 may associate the attaching angle $\theta_1'$ described in the other second embodiment with the arithmetic parameter of the arithmetic processing determined according to the attaching angle $\theta_1'$. Thus, the control processing unit 32 can easily compare and use the measurement results regardless of the orientation of the sensor 200.

Although the present disclosure has been described as a hardware configuration in the above embodiments, the present disclosure is not limited to this. According to the present disclosure, each of the processing related to the motion state monitoring method can be implemented by causing the processor to execute a computer program, for example, a motion state monitoring program.

In the embodiments described above, the computer is composed of a computer system including a personal computer, a word processor, etc. However, the computer is not limited to this and may be constituted by a LAN server, a host of computer (personal computer) communication, a computer system connected to the Internet, or the like. The functions may be distributed to devices on the network and a whole network may serve as a computer.

FIG. 10 is a schematic configuration diagram of a computer 1900 according to the above embodiments. The computer 1900 includes a processor 1010, a ROM 1020, a RAM 1030, an input apparatus 1050, a display apparatus 1100, a storage apparatus 1200, a communication control apparatus 1400, and an input/output I/F 1500, which are connected through a bus line such as a data bus.

The processor 1010 implements various controls and calculations according to programs stored in various storage units such as the ROM 1020 and the storage apparatus 1200. The processor 1010 may be a CPU (Central Processing Unit), a GPU (Graphics Processing Unit), an FPGA (Field-Programmable Gate Array), a DSP (Digital Signal Processor), an ASIC (Application Specific Integrated Circuit), or the like.

The ROM 1020 is a read-only memory in which various programs and data for the processor 1010 to perform various controls and calculations are stored in advance.

The RAM 1030 is a random access memory used as working memory by the processor 1010. In the RAM 1030, various areas for performing various processes according to the above-described embodiment can be secured.

The input apparatus 1050 is, for example, a keyboard, a mouse, or a touch panel that receives an input from the user.

The display apparatus 1100 displays various screens under the control of the processor 1010. The display apparatus 1100 may be a liquid crystal panel, an organic EL (electroluminescence), an inorganic EL, or the like. The display apparatus 1100 may be a touch panel serving also as the input apparatus 1050.

The storage apparatus 1200 is a storage medium including a data storage unit 1210 and a program storage unit 1220. The program storage unit 1220 stores programs for implementing various processes in the above-described embodiments. The data storage unit 1210 stores various data of various databases according to the above-described embodiments.

A storage medium of the storage apparatus 1200 may be a non-transitory computer readable medium. The program includes instructions (or software codes) that, when loaded into a computer, cause the computer to perform one or more of the functions described in the embodiments. The program may be stored in a non-transitory computer readable medium or a tangible storage medium. By way of example, and not a limitation, non-transitory computer readable media or tangible storage media can include a random-access memory (RAM), a read-only memory (ROM), a flash memory, a solid-state drive (SSD) or other types of memory technologies, a CD-ROM, a digital versatile disc (DVD), a Blu-ray disc or other types of optical disc storage, and magnetic cassettes, magnetic tape, magnetic disk storage or other types of magnetic storage devices. The program may be transmitted on a transitory computer readable medium or a communication medium. By way of example, and not a limitation, transitory computer readable media or communication media can include electrical, optical, acoustical, or other forms of propagated signals.

When the computer 1900 executes various kinds of processing, it reads the program from the storage apparatus 1200 into the RAM 1030 and executes it. However, the computer 1900 can read and execute the program directly from an external storage medium into the RAM 1030. In some computers, various programs and the like may be stored in the ROM 1020 in advance and executed by the processor 1010. In addition, the computer 1900 may download and execute various programs and data from other storage media through the communication control apparatus 1400.

The communication control apparatus 1400 is for network connection between the computer 1900 and another external computer. The communication control apparatus 1400 allows these external computers to access the computer 1900.

The input/output I/F 1500 is an interface for connecting various input/output devices through a parallel port, a serial port, a keyboard port, a mouse port or the like.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A method comprising:
acquiring, by a processor, sensing information of a sensor attached to a target part of a body of a subject, the sensing information including quaternion information;
detecting, by the processor, an attaching direction of the sensor based on the sensing information with respect to a reference direction defined based on the target part, wherein the reference direction remains the same relative to the target part when a position of the sensor with respect to the target part changes, the reference direction defined as an axial direction of a band attached to the target part;
executing, by the processor, tagging processing for associating the attaching direction of the sensor with sensing-related information related to the sensing information, the sensing-related information including the sensing information and information obtained by converting the quaternion information into rotation angle information;
calculating, by the processor, a motion state of the target part based on the sensing-related information tagged with the attaching direction;
outputting, by the processor, the calculated motion state of the target part with an indication of relation to the attaching directions;
determining, by the processor, that an attaching direction changing event has occurred based on a difference of attaching directions measured before and after a predetermined timing; and
updating, by the processor, based on determining that the attaching direction changing event has occurred, the attaching direction of the sensor.

2. The method according to claim 1, wherein
the outputting includes executing arithmetic processing on the sensing information or the sensing-related information in accordance with the attaching direction, and outputting a result of the arithmetic processing.

3. The method according to claim 1, further comprising:
calculating a motion state index indicating the motion state of the target part based on the sensing-related information.

4. The method according to claim 3, wherein the motion state index is a three-dimensional rotation angle of the target part.

5. The method according to claim 1, wherein
the outputting includes displaying an image representing an attaching position of the sensor on the target part.

6. The method according to claim 5, wherein
the outputting includes displaying the image representing the attaching direction of the sensor on the attaching position in response to selection of the image representing the attaching position.

7. The method according to claim 1, further comprising:
acquiring, by the processor, additional sensing information of an additional sensor attached to an additional target part of the body of the subject, the additional sensing information including additional quaternion information;
detecting, by the processor, an additional attaching direction of the additional sensor with respect to an additional reference direction defined based on the additional target part, wherein the additional reference direction remains the same relative to the additional target part when a position of the additional sensor with respect to the additional target part changes;
executing, by the processor, tagging processing for associating the additional attaching direction of the additional sensor with additional sensing-related information related to the additional sensing information, the additional sensing-related information including the additional sensing information and additional information obtained by converting the additional quaternion information into rotation angle information
calculating, by the processor, a motion state index of the target part based on an information difference between the quaternion information of the sensor and the additional quaternion information of the additional sensor, wherein the motion state index is a three-dimensional angle of the target part; and
outputting, by the processor, the motion state index.

8. A system comprising:
at least one memory storing instructions, and
at least one processor configured to execute the instructions to:
acquire sensing information of a sensor attached to a target part of a body of a subject, the sensing information including quaternion information;
detect an attaching direction of the sensor with respect to a reference direction defined based on the target part, wherein the reference direction remains the same relative to the target part when a position of the sensor with respect to the target part changes, the reference direction defined as an axial direction of a band attached to the target part;
execute tagging processing for associating the attaching direction of the sensor with sensing-related information related to the sensing information, the sensing-related information including the sensing information and information obtained by converting the quaternion information into rotation angle information;
calculate a motion state of the target part based on the sensing-related information tagged with the attaching direction;
output the calculated motion state of the target part with an indication of relation to the attaching direction;
determine that an attaching direction changing event has occurred based on a difference of attaching directions measured before and after a predetermined timing; and
update the attaching direction of the sensor based on determining that the attaching direction changing event has occurred.

9. A training support system comprising:
the system according to claim 8; and
measuring equipment including the sensor.

10. The training support system according to claim 9, wherein
the measuring equipment includes a handle configured to change the attaching direction of the sensor.

11. A non-transitory computer readable medium storing a program causing a computer to execute:
a step of acquiring sensing information of a sensor attached to a target part of a body of a subject, the sensing information including quaternion information;
a step of detecting an attaching direction of the sensor in a stationary state with respect to a reference direction defined based on the target part, wherein the reference direction remains the same relative to the target part when a position of the sensor with respect to the target part changes, the reference direction defined as an axial direction of a band attached to the target part;

a step of executing tagging processing for associating the attaching direction of the sensor with sensing-related information, the sensing-related information including the sensing information and information obtained by converting the quaternion information into rotation angle information;

a step of calculating a motion state of the target part based on the sensing-related information tagged with the attaching direction;

a step of outputting the calculated motion state of the target part with an indication of relation to the attaching directions;

a step of determining that an attaching direction changing event has occurred based on a difference of attaching directions measured before and after a predetermined timing, and a step of updating the attaching direction of the sensor based on determining that the attaching direction changing event has occurred.

* * * * *